US00PP20810P2

(12) United States Plant Patent
Jacobs

(10) Patent No.: US PP20,810 P2
(45) Date of Patent: Mar. 9, 2010

(54) ***ALSTROEMERIA* PLANT NAMED 'ZALSASAQ'**

(50) Latin Name: *Alstroemeria hybrida*
Varietal Denomination: Zalsasaq

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 0 days.

(21) Appl. No.: 12/291,384

(22) Filed: Nov. 7, 2008

(51) Int. Cl.
*A01H 5/00* (2006.01)

(52) U.S. Cl. ..... Plt./309

(58) Field of Classification Search ..... Plt./309
See application file for complete search history.

(56) References Cited

OTHER PUBLICATIONS

UPOV-ROM PBR 20071694, published Oct. 15, 2007.*

* cited by examiner

*Primary Examiner*—June Hwu
*Assistant Examiner*—Louanne C Krawczewicz Myers
(74) *Attorney, Agent, or Firm*—C. A. Whealy

(57) ABSTRACT

A new and distinct cultivar of *Alstroemeria* plant named 'Zalsasaq', characterized by its erect and strong flowering stems; vigorous growth habit; salmon orange-colored flowers; and excellent postproduction longevity.

1 Drawing Sheet

Botanical designation: *Alstroemeria hybrida.*
Cultivar denomination: 'Zalsasaq'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Zalsasaq'.

The new *Alstroemeria* plant is a naturally-occurring whole plant mutation of *Alstroemeria hybrida* 'Staqueen', disclosed in U.S. Plant Pat. No. 14,335. The new *Alstroemeria* was discovered and selected by the Inventor as a flowering plant from within a population of plants of 'Staqueen' in a controlled greenhouse environment in Rijsenhout, The Netherlands in June, 2005.

Asexual reproduction of the new *Alstroemeria* plant by rhizome divisions in a controlled greenhouse environment in Rijsenhout, The Netherlands since September, 2005, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zalsasaq'. These characteristics in combination distinguish 'Zalsasaq' as a new and distinct cultivar of *Alstroemeria* plant:

1. Erect and strong flowering stems.
2. Vigorous growth habit.
3. Salmon orange-colored flowers.
4. Excellent postproduction longevity.

Plants of the new *Alstroemeria* can be compared to plants of the parent, 'Staqueen'. Plants of the new *Alstroemeria* differ from plants of 'Staqueen' primarily in flower color as plants of the new *Alstroemeria* have lighter-colored flowers than plants of 'Staqueen'.

Plants of the new *Alstroemeria* can be compared to plants of *Alstroemeria hybrida* 'Zalsasenan', disclosed in U.S. Plant Pat. No. 15,274. In side-by-side comparisons conducted in Rijsenhout, The Netherlands, plants of the new *Alstroemeria* differed primarily from plants of 'Zalsasenan' in flower color as plants of 'Zalsasenan' have intense yellow-colored flowers.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria.*

The photograph comprises a side perspective view of a typical flowering stem of 'Zalsasaq'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15° C. to 20° C., night temperatures ranged from 10° C. to 15° C. and light levels averaged 5,000 lux. Plants used for the photograph and description had been growing for one year. The photograph and the description were taken in the late summer. Color references are made to The Royal Horticultural Society Colour Chart, 1995 Edition, except where general terms of ordinary dictionary significance are used.

Botanical classification: *Alstroemeria hybrida* 'Zalsasaq'.

Parentage: Naturally-occurring whole plant mutation of *Alstroemeria hybrida* 'Staqueen', disclosed in U.S. Plant Pat. No. 14,335.

Propagation:

*Type.*—By tissue culture.

*Time to produce a rooted young plant, summer.*—About 40 days.

*Time to produce a rooted young plant, winter.*—About 60 days.

*Root description.*—Fibrous, fleshy, thick; close to 155D in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright; freely branching, bushy appearance; vigorous growth habit.

*Time from planting to harvest of cut flowers.*—About 80 to 90 days.

*Number of flowering stems produced per year.*—About 180 to 260.

*Plant height.*—About 125 cm to 145 cm.

*Plant diameter* (*spread*).—About 35 cm.

Flowering stem description:

*Aspect.*—Erect.

*Length.*—About 107 cm to 125 cm.

*Diameter.*—About 7 mm to 9 mm.

*Internode length.*—About 5 cm to 11 cm.

*Strength.*—Strong.

*Texture.*—Smooth, glabrous.

*Color.*—Close to 146C; tinted with close to 187A.

Foliage description:

*Appearance.*—Leaves asymmetrical; sessile.

*Length.*—About 16.8 cm to 20.2 cm.

*Width.*—About 2.8 cm to 3.8 cm.

*Shape.*—Lanceolate to oblong.

*Apex.*—Acute.

*Base.*—Attenuate.

*Margin.*—Entire; slightly undulate.

*Texture, upper and lower surfaces.*—Smooth, glabrous.

*Venation pattern.*—Parallel.

*Color.*—Developing and fully developed leaves, upper surface: Close to 147A; venation, close to 147A. Developing and fully developed leaves, lower surface: Close to 137B; venation, close to 137B.

Flower description:

*Flower type and habit.*—Single cup-shaped flowers arranged in compound umbels. Flowers face mostly outwardly. Perianth segments separate. Freely and continuously flowering.

*Natural flowering season.*—Flowering continuous during the spring in The Netherlands.

*Fragrance.*—Not detected.

*Flower longevity on the plant.*—About four weeks; flowers not persistent.

*Flower longevity as a cut flower.*—About 12 to 16 days.

*Flower buds* (*showing color*).—Length: About 4.5 cm to 5.5 cm. Diameter: About 1.5 cm to 1.8 cm. Shape: Roughly ovoid. Color: Close to 168B.

*Umbel height.*—About 16.5 cm to 21 cm.

*Umbel diameter.*—About 20 cm to 23 cm.

*Number of flowers per umbel.*—About 6 to 32.

*Flower diameter.*—About 7.5 cm to 8.5 cm.

*Flower length* (*height*).—About 7.5 cm to 8.5 cm.

*Flower depth.*—About 7 cm to 8 cm.

*Perianth.*—Arrangement: Six arranged in two whorls, each whorl with two lateral and one median segments. Outer perianth, lateral segments: Length: About 6.8 cm to 7 cm. Width: About 3.4 cm to 3.6 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 24B; central blotch, close to 25A; towards the apex, greenish overtones. Color, when opening and fully opened, lower surface: Close to 24C; central blotch, close to 32B; towards the apex and venation, greenish overtones. Outer perianth, median segment: Length: About 7.2 cm to 7.5 cm. Width: About 3.5 cm to 3.7 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 24B; central blotch, close to 25A and 13A; towards the apex, greenish overtones. Color, when opening and fully opened, lower surface: Close to 24C; central blotch, close to 32B; towards the apex and venation, greenish overtones. Inner perianth, lateral segments: Length: About 7.2 cm to 7.5 cm. Width: About 2 cm to 2.2 cm. Shape: Oblanceolate. Apex: Wishbone-shaped. Base: Attenuate. Margin: Entire; weakly undulate. Texture, upper and lower surfaces: Smooth, glabrous. Color, when opening and fully opened, upper surface: Close to 24B; central blotch, close to 25A; towards the base, close to 12A; stripes, close to 183A. Color, when opening and fully opened, lower surface: Close to 24C; central blotch, close to 32B; venation, greenish overtones; occasional stripes, close to 183A. Inner perianth, median segment: Length: About 5.9 cm to 6.2 cm. Width: About 1.9 cm to 2.1 cm. Shape: Oblanceolate. Apex: Wishbone-shaped. Base: Attenuate. Margin: Entire; weakly undulate. Texture, upper and lower surfaces: Smooth, glabrous. Color, when opening and fully opened, upper surface: Close to 24B; central blotch, close to 25A; stripes, close to 183A. Color, when opening and fully opened, lower surface: Close to 24C; central blotch, close to 32B; venation, greenish overtones; occasional stripes, close to 183A.

*Pedicels: Length: About* 7.5 to 12.5 cm. Diameter: About 3 mm. Strength: Strong. Angle: Erect to about 20° C. from vertical. Texture: Smooth, glabrous. Color: Close to 146B tinted with close to 187A.

*Reproductive organs.*—Stamens: Quantity per flower: Six. Anther shape: Elliptical. Anther length: About 9 mm. Anther diameter: About 3 mm. Anther color: Close to 152C. Pollen amount: Scarce. Pollen color: Close to 163B. Pistils: Quantity per flower: One. Style length: About 4 cm to 4.5 cm. Style color: Close to 170B. Stigma color: Close to 170C. Ovary color: Close to 146B tinted with close to 166A.

*Fruit/seed.*—Fruit and seed development has not been observed.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from about −5° C. to about 40° C.

It is claimed:

1. A new and distinct *Alstroemeria* plant named 'Zalsasaq' as illustrated and described.

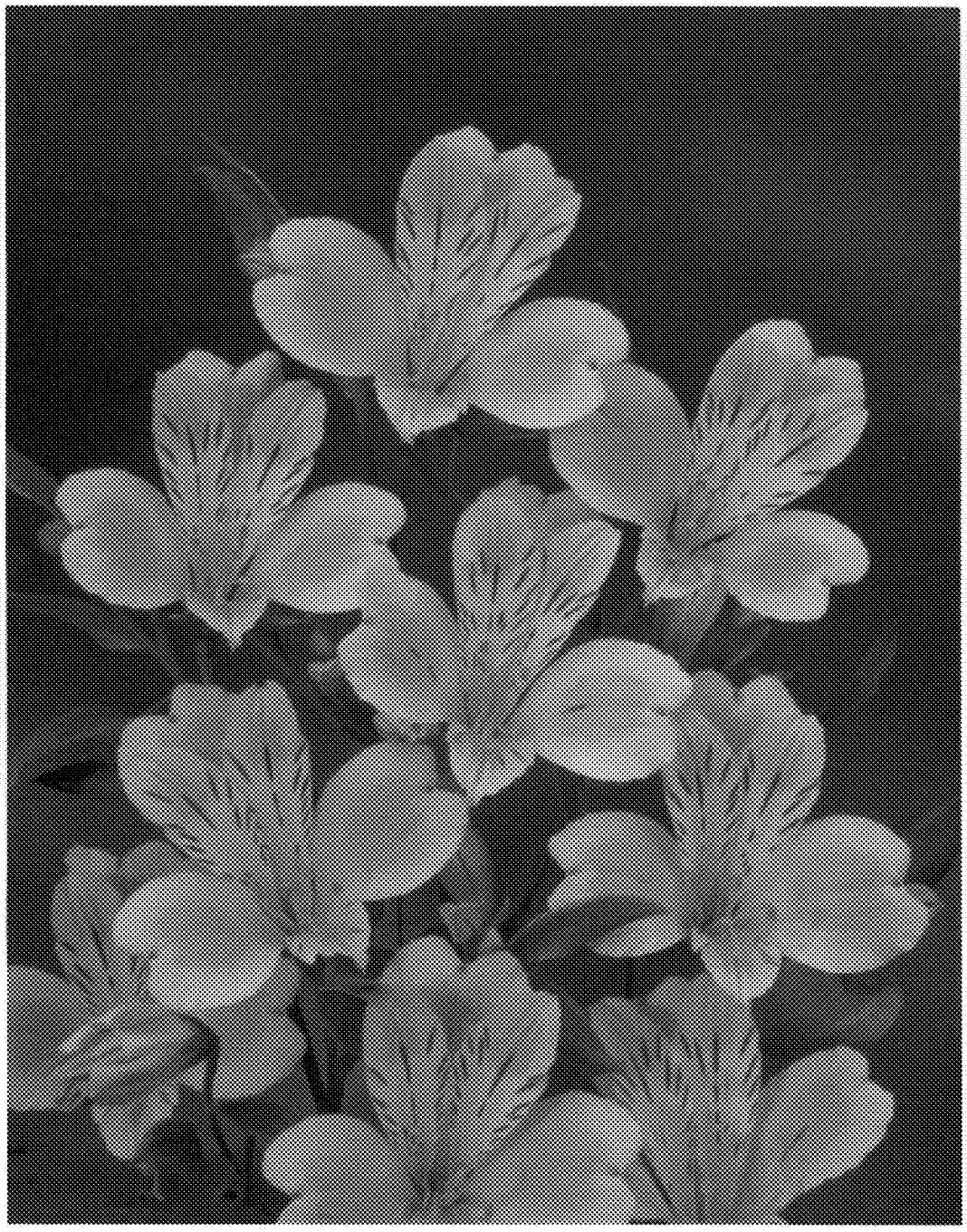

* * * * *